United States Patent
Siegner

(10) Patent No.: US 8,231,561 B2
(45) Date of Patent: Jul. 31, 2012

(54) UNDER CAST AIR SLEEVE

(75) Inventor: Kenneth Scott Siegner, Calimesa, CA (US)

(73) Assignee: Anodyne Medical Device, Inc., Coral Springs, FL (US)

( * ) Notice: Subject to any disclaimer, the term of this patent is extended or adjusted under 35 U.S.C. 154(b) by 200 days.

(21) Appl. No.: 12/814,856

(22) Filed: Jun. 14, 2010

(65) Prior Publication Data

US 2011/0306910 A1  Dec. 15, 2011

(51) Int. Cl.
*A61F 5/00* (2006.01)
(52) U.S. Cl. .................................. 602/13; 128/DIG. 20
(58) Field of Classification Search .................... 602/13; 128/DIG. 20; 601/6, 11, 12
See application file for complete search history.

(56) References Cited

U.S. PATENT DOCUMENTS

| | | | |
|---|---|---|---|
| 3,908,642 A | 9/1975 | Vinmont | |
| 5,846,063 A * | 12/1998 | Lakic | 417/440 |
| 6,014,823 A * | 1/2000 | Lakic | 36/93 |
| 6,053,882 A | 4/2000 | Johansen | |
| 7,229,425 B2 | 6/2007 | Dunagan | |
| 7,250,034 B2 | 7/2007 | Barberio | |
| 7,497,838 B1 | 3/2009 | Dunagan | |
| 7,591,796 B1 * | 9/2009 | Barak et al. | 601/152 |

* cited by examiner

*Primary Examiner* — Michael A. Brown
(74) *Attorney, Agent, or Firm* — Nixon & Vanderhye P.C.

(57) ABSTRACT

An air sleeve for stimulating blood flow and providing aeration around, under and within a cast includes a base film with an array of nodal air cells, at least some of which are perforated on a skin side of the base film. A spacer fabric layer, which is at least partially air permeable, is disposed on the skin side of the base film, and a valve is extendable through the cast and is in fluid communication with the air cells.

20 Claims, 5 Drawing Sheets

UNDER CAST AIR SLEEVE

CROSS-REFERENCES TO RELATED APPLICATIONS (NOT APPLICABLE)

STATEMENT REGARDING FEDERALLY SPONSORED RESEARCH OR DEVELOPMENT (NOT APPLICABLE)

BACKGROUND OF THE INVENTION

The invention relates to an air sleeve to be secured against a wearer's skin underneath a plaster cast or the like and, more particularly, to an air sleeve that includes structure for stimulating the area inside the cast and for circulating air inside the cast to aerate the skin.

It is typical to apply a plaster cast or the like to a broken limb to immobilize the limb and encourage proper healing. Due to the immobility of the limb, however, the area within the cast has limited blood flow. The limited blood flow can cause discomfort to the patient such as numbness, tingling, pain, etc.

Additionally, the patient's skin under the cast has limited aeration, and the skin can deteriorate. The environment could also lead to patient discomfort including itching and sores and the like as well as compromising skin pigmentation and overall skin health.

BRIEF SUMMARY OF THE INVENTION

It would be desirable to provide a sleeve or liner in contact with the patient's skin prior to forming the cast that is capable of overcoming the noted drawbacks associated with a conventional cast. An air sleeve may include a plurality of nodal air cells in fluid communication with a plumbing feature connectable to a pump. The pump serves to inflate the nodal cells to thereby stimulate the area under the cast. At least some of the cells are provided with perforations on a skin side, and air from the inflated cells can bleed through the side of the nodes facing the skin to thereby cool and aerate the skin.

In an exemplary embodiment, an air sleeve for stimulating blood flow and providing aeration around, under and within a cast includes a base film with an array of nodal air cells, at least some of which are perforated on a skin side of the base film. A spacer fabric layer, which is at least partially air permeable, is disposed on the skin side of the base film, and a valve is extendable through the cast and is in fluid communication with the air cells. The spacer fabric layer preferably defines an air passage that permits air circulation around and through a complete length of the air sleeve. In one arrangement, the array of nodal air cells includes a matrix of air cells including rows and columns. In this context, alternating ones of the nodal air cells along the rows and columns are perforated. Moreover, the valve may be a first valve in fluid communication with a first set of the alternating nodal air cells, where the air sleeve additionally includes a second valve in fluid communication with a second set of the alternating nodal air cells.

An air manifold communicating with the valve may be interposed between the valve and the air cells. The air manifold includes at least a first tubing in fluid communication with a first set of the air cells and a second tubing in fluid communication with a second set of the air cells. The air manifold may additionally include structure, such as a rotary valve, for alternating a coupling between the valve and the first and second tubing, respectively. The alternating structure may alternatively include a timer for switching the coupling between the valve and the first and second tubing, respectively.

The air sleeve may additionally include a portable pump connected to the valve.

The air cell perforations are preferably sized to permit inflation of the air cells and a slow air bleed on the skin side of the base film. Preferably, the air cell perforations vary in size, where the air cell array is configured to deliver evenly distributed pressure variations without lines or ridges of high pressure.

A connector may be secured at one end of the air sleeve and removably attachable to an opposite end of the air sleeve, allowing for a universal sleeve adjustable for a range of limb sizes.

In another exemplary embodiment, an air sleeve for stimulating blood flow and providing aeration around, under and within a cast includes facing sheets of film that are RF welded together to define an array of nodal air cells connected via integrated plumbing channels. At least some of the air cells are perforated on a skin side of the facing sheets. A plumbing fitting is extendable through the cast and in fluid communication with the air cells via the integrated plumbing channels.

In yet another exemplary embodiment, a method for stimulating blood flow and providing aeration around, under and within a cast using the air sleeve of the invention includes the steps of (a) connecting a pump to the valve; (b) inflating the air cells; and (c) bleeding air through the perforations and the spacer fabric layer to aerate a wearer's skin inside the case. In one embodiment, the pump is portable, and the method includes the step of repeating steps (b)-(c) in a continuous cycle.

BRIEF DESCRIPTION OF THE DRAWINGS

These and other aspects and advantages will be described in detail with reference to the accompanying drawings, in which.

DETAILED DESCRIPTION OF THE INVENTION

Figure 1:
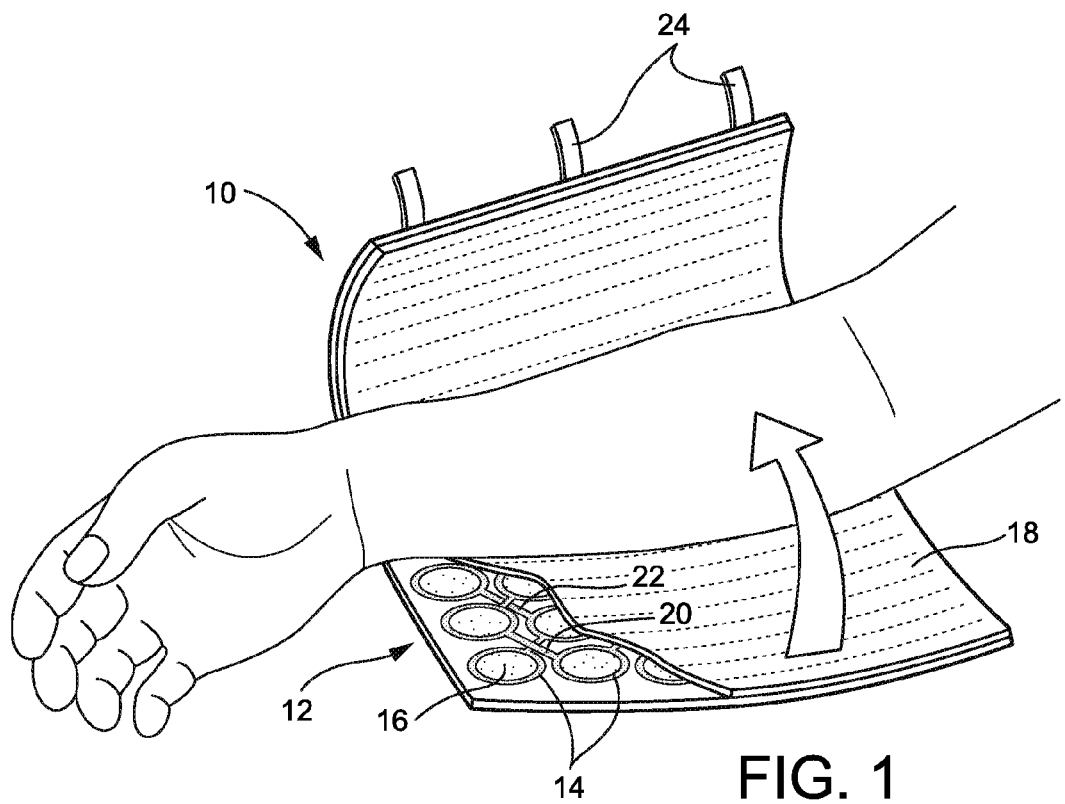
FIG. 1 is a perspective view of the air sleeve prior to installation.
Figure 1A:
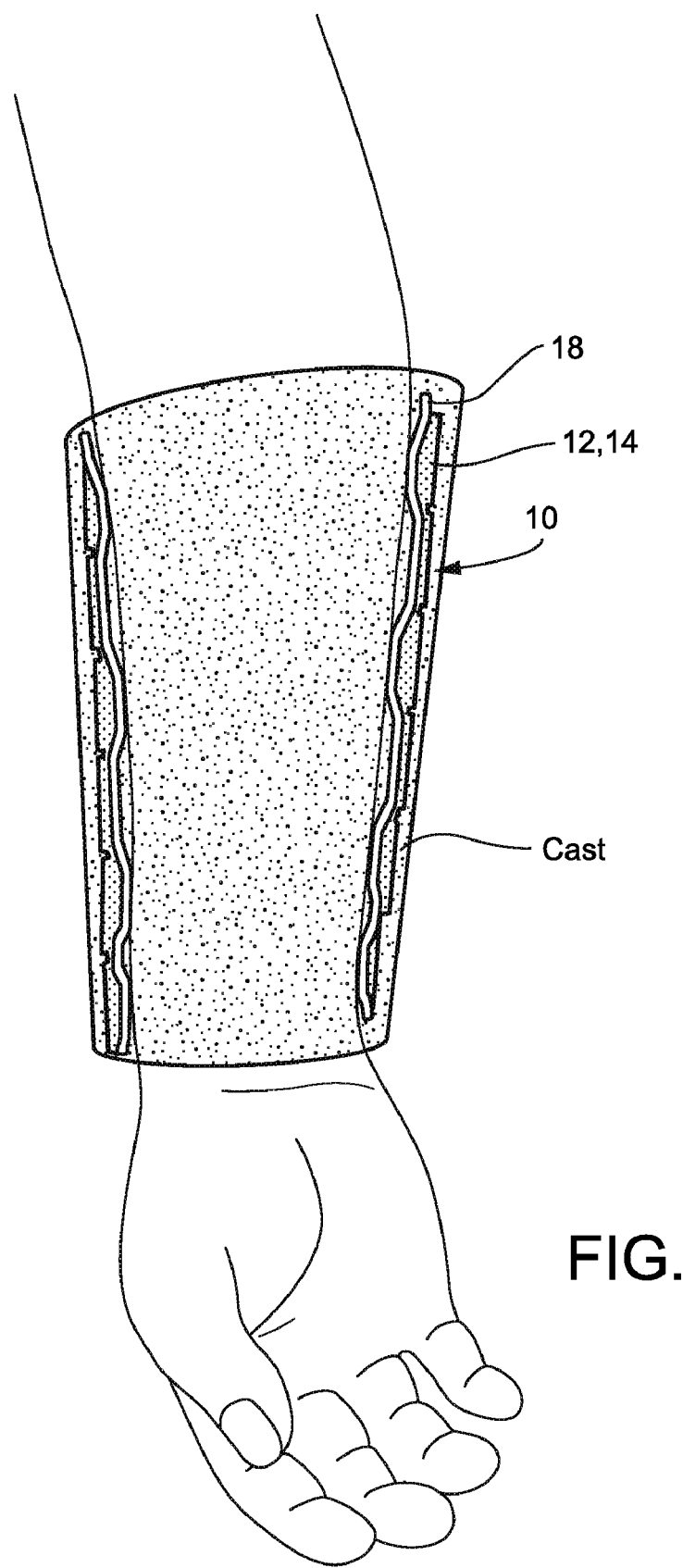
FIG. 1A shows an air sleeve under a hard cast.

FIG. 1 shows an air sleeve 10 being applied to an arm, and FIG. 1A shows the air sleeve under a hard cast. The air sleeve 10 is positioned prior to installation of a hard cast or the like in direct contact with the wearer's skin. A base film 12 includes an array of nodal air cells 14, at least some of which include perforations 16 on a skin side thereof. In an exemplary construction, the base film 12 is formed with two layers of film, preferably urethane, that are welded in a flat (non-vacuum formed state) via RF welding in a welding die or the like. With the film layers properly oriented, the layers are welded to define the nodal air cell array 14.

A spacer fabric layer 18 formed of a soft at least partially air-permeable material is interposed between the base film 12 and the wearer's skin (see also, FIG. 1A). By virtue of the spacer fabric layer 18, air passages are always present and open allowing air to fully circulate all around and through the complete length of the air sleeve 10, with no pressure ridges. This structure provides excellent air circulation for improved blood flow and skin condition. Suitable materials for the spacer fabric 18 include, for example, polyester, nylon and like materials. The spacer fabric layer 18 is preferably about $\frac{1}{8}^{th}$ inch thick, although other thicknesses may be suitable. Preferably, a second spacer fabric layer may be provided on an outside surface of the base film 12.

As shown in FIG. 1, the array of nodal air cells 14 is formed as a matrix of air cells including rows and columns. In an exemplary embodiment, alternating ones of the nodal air cells 14 are formed via welding such that they are fluidly connected by links 20. A second set of air cells 14 is similarly connected via links 22. With separately defined sets of air cells 14, the pressure in each set can be alternated to provide a massaging effect on the wearer's limb. Preferably, the air cells 14 include perforations 16 that are sized to permit initial inflation of the air cells 14 and a slow air bleed on the skin side of the base film 12. The initial inflation of the air cells 14 stimulates the area under the cast, and the air bleeding through the perforations 16 circulates through the spacer fabric 18 to dry and aerate the skin.

A connector 24 such as butterfly fasteners, adhesive, hook and loop fasteners, or the like secures the air sleeve in place during and after installation of the hard cast. An adhesive or like connector may alternatively or additionally be provided on an overlapping surface of the spacer fabric 18. These fasteners allow for a universal wrap of the sleeve to be used for all limb diameters and proper fit. The air sleeve is thus readily adjustable to accommodate varying limb sizes.

Figure 2:
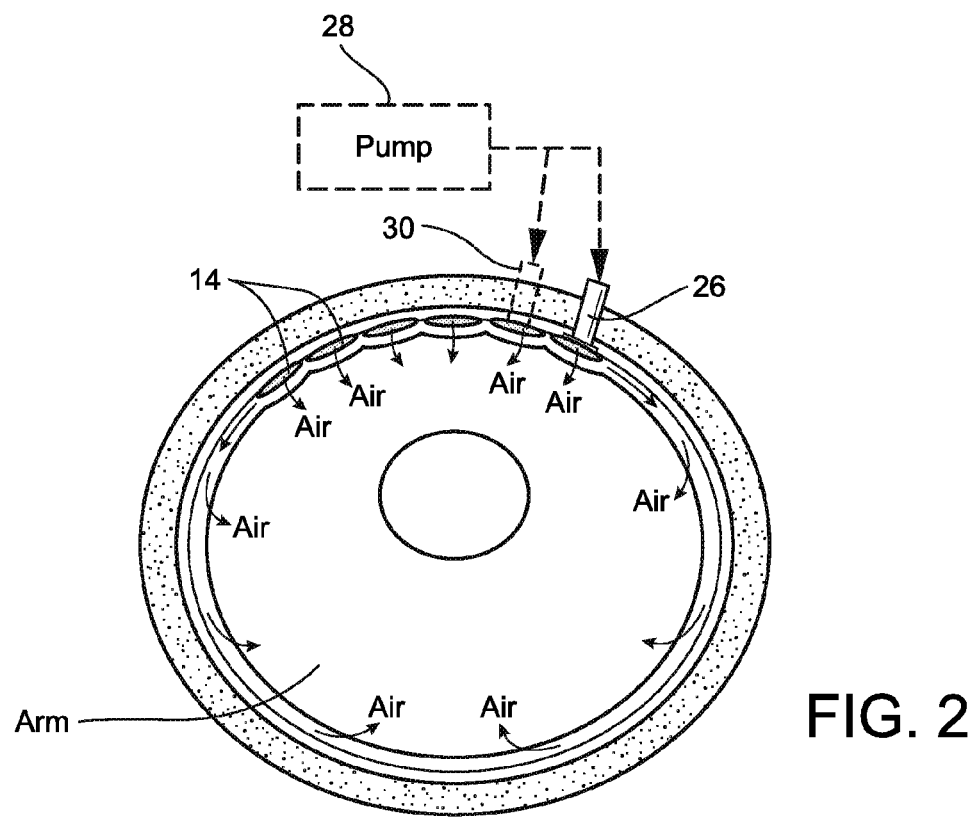
FIG. 2 is a cross section through a broken limb with the air sleeve under a hard cast.

FIG. 2 is a cross section showing a limb wrapped with the air sleeve 10 inside a hard cast. The air sleeve 10 is provided with a plumbing fitting, such as a valve 26 as shown, around which the hard cast is formed such that the valve 26 extends through the cast. The valve 26 is in fluid communication with the air cells 14. In use, the wearer can secure a pump 28 to the valve 26 to provide a burst or pulsation of pressurized air to inflate the nodal air cells 14. A portable pump 28 may form part of the device. As noted above, inflation of the nodal cells 14 stimulates the area under the cast and circulates air through the spacer fabric 18 to dry and aerate the skin. If the nodal air cells 14 are arranged as two separate sets of air cells, a second valve 30 in fluid communication with a second set of air cells may also be provided.

Figure 3:
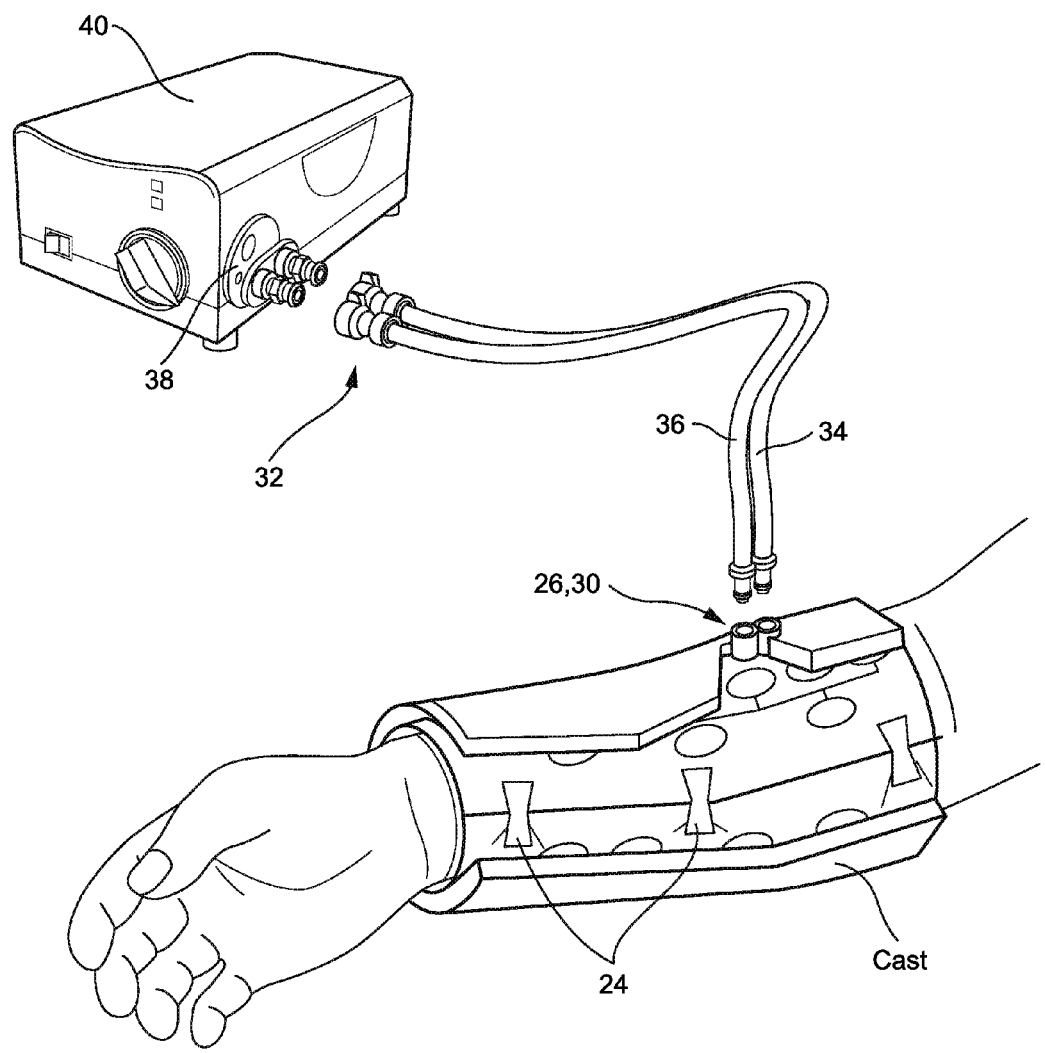
FIG. 3 shows an air manifold interposed between the plumbing feature and the air cells.

As an alternative construction, with reference to FIG. 3, an air manifold 32 communicates with the valves 26, 30, which deliver air to the air cells 14. The air manifold 32 can include at least a first tubing 34 in fluid communication with the first set of air cells, and a second tubing 36 in fluid communication with the second set of air cells. The manifold 32 may also include structure for alternating a coupling between the valves 26, 30 and the first and second tubing 34, 36, respectively. Any suitable structure for this purpose may be used. Exemplary structure may include a rotary valve 38 connected with pump 40 including a timer, or the timer can form part of a processor that controls the pump 40 and manifold 32. The pump delivers air to one channel/tube 34, 36 at a time. When it is time for the other channel to be pressurized, the rotary valve 38 turns and allows the existing pressurized channel to bleed back through the pump 40 while pressurizing the other channel.

Figure 4:
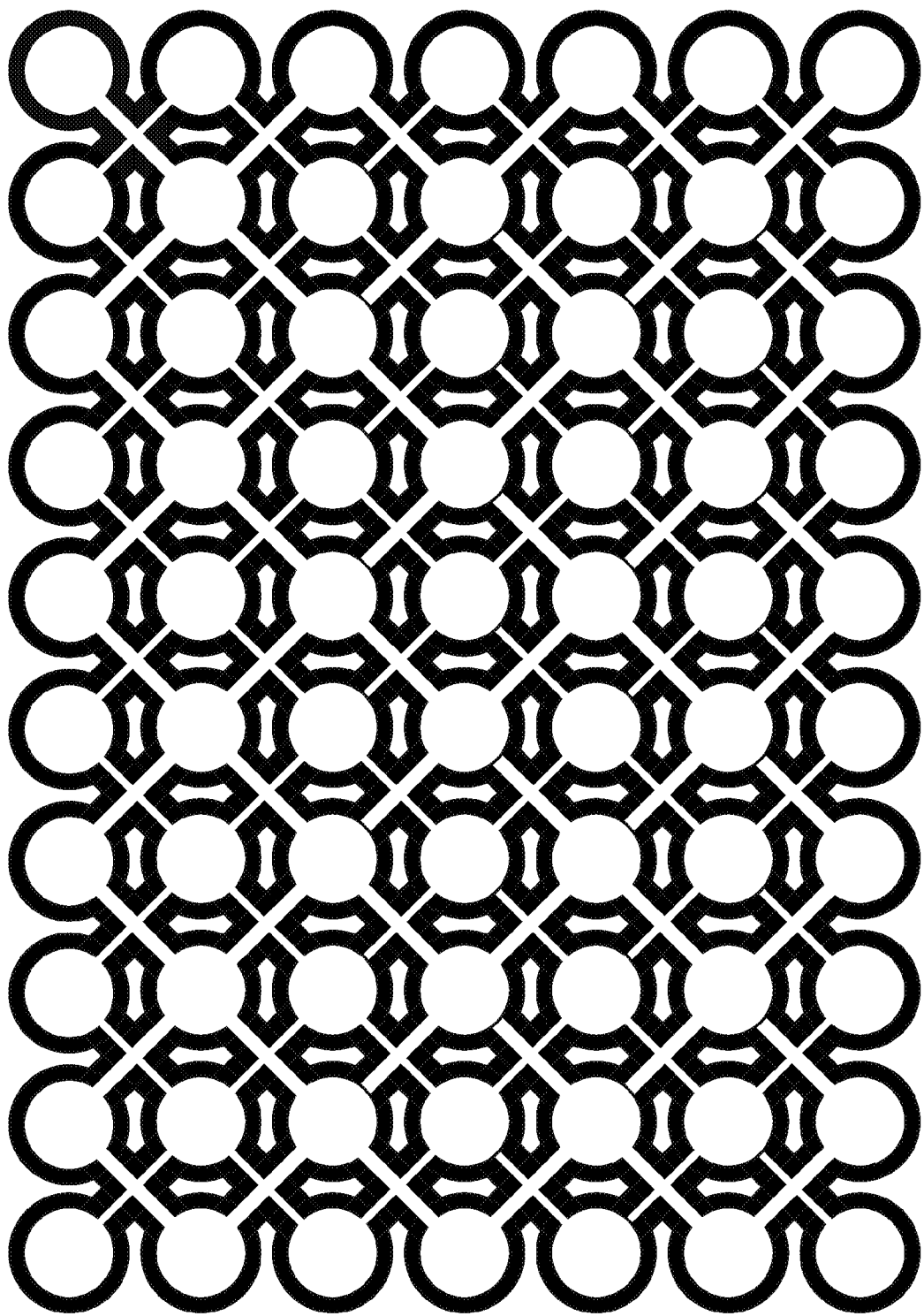
FIG. 4 shows an exemplary sleeve pattern for a small single channel pump.
Figure 5:
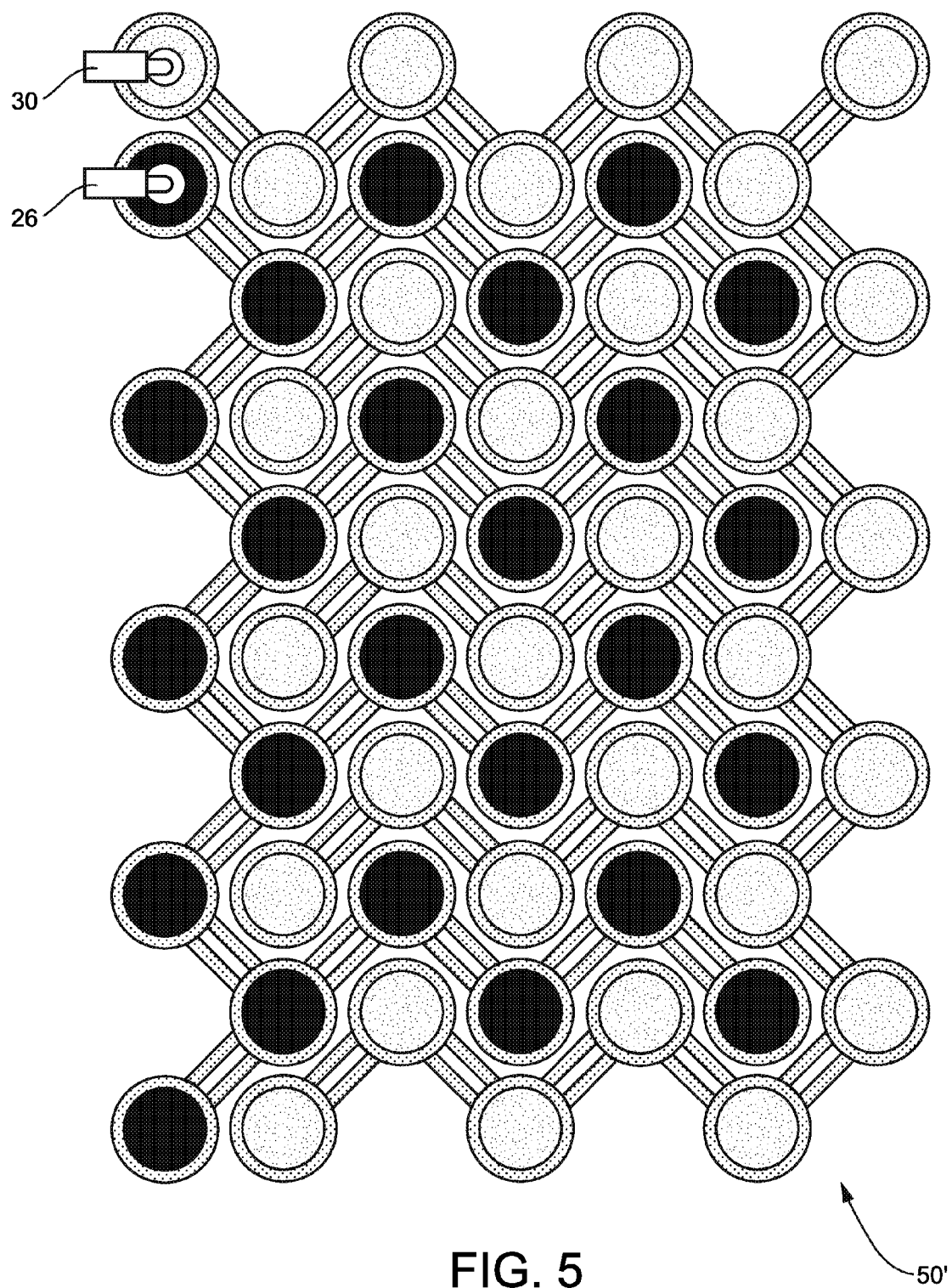
FIG. 5 shows an exemplary pattern for a two-channel pump.

FIGS. 4 and 5 show exemplary sleeve patterns 50, 50'. The pattern 50 in FIG. 4 is suitable for a pump that is relatively small and provides a single channel of operation. The pump in this application would be portable and could be affixed to the cast or worn on a clip with a belt or the like. Preferably, half of the channels have a constricted (narrow) flow path. The circular feature in these paths has a perforation to bleed the air continuously while there is air in the system. The circular feature in the path of the wider openings provides more exaggerated deformation to the bladder, which would provide the stimulation. The idea is that if a wider unconstricted path allows greater deformation, and a restricted (narrower) path allows a continuous bleed of air, both benefits (stimulation and aeration) can be achieved with a single channel system. Additionally, the lack of valves equals a smaller, less expensive and more convenient pump system.

The pattern 50' in FIG. 5 shows dark and light colored circular cells and is designed to accommodate a two channel pump to deliver alternating pressure therapy, which stimulates the limb and provides for better blood flow. This system would preferably include a pump with valves 26, 30 and the ability to cycle in variable time sequences. Generally, this system might be used at a bedside with patients. The design provides more adjustability and independent controls to the system.

With the exemplary cell patterns shown in FIGS. 4 and 5, lines or ridges of high pressure, which may cut off blood flow, are avoided. The cells, including some with smaller holes while others have larger holes to allow for aeration and stimulation, respectively, rather deliver evenly distributed pressure variations.

With air sleeve of the described embodiments, circulation to an area inside a hard cast can be stimulated, thereby preventing at least some of the discomfort of wearing a hard cast. Additionally, enabling air to circulate across the skin under the cast improves skin health during healing and further reduces discomfort associated with wearing a cast.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. An air sleeve for stimulating blood flow and providing aeration around, under and within a cast, the air sleeve comprising:
    a base film including an array of nodal air cells, at least some of the air cells being perforated on a skin side of the base film;
    a spacer fabric layer disposed on the skin side of the base film, the spacer fabric being at least partially air permeable; and
    a valve extendable through the cast and in fluid communication with the air cells.

2. An air sleeve according to claim 1, wherein the array of nodal air cells comprises a matrix of air cells including rows and columns, and wherein alternating ones of the nodal air cells along the rows and columns are perforated.

3. An air sleeve according to claim 2, wherein the valve is a first valve in fluid communication with a first set of the alternating nodal air cells, and wherein the air sleeve further comprises a second valve in fluid communication with a second set of the alternating nodal air cells.

4. An air sleeve according to claim 1, wherein the valve is a first valve in fluid communication with a first set of the nodal air cells, and wherein the air sleeve further comprises a second valve in fluid communication with a second set of the nodal air cells.

5. An air sleeve according to claim 1, further comprising an air manifold communicating with the valve and interposed between the valve and the air cells, the air manifold including at least a first tubing in fluid communication with a first set of the air cells and a second tubing in fluid communication with a second set of the air cells.

6. An air sleeve according to claim 5, wherein the air manifold comprises means for alternating a coupling between the valve and the first and second tubing, respectively.

7. An air sleeve according to claim 6, wherein the alternating means comprises a rotary valve.

8. An air sleeve according to claim 6, wherein the alternating means comprises a timer for switching the coupling between the valve and the first and second tubing, respectively.

9. An air sleeve according to claim 1, further comprising a portable pump connected to the valve.

10. An air sleeve according to claim 1, wherein the air cell perforations are sized to permit inflation of the air cells and a slow air bleed on the skin side of the base film.

11. An air sleeve according to claim 1, further comprising a connector secured at one end of the air sleeve and removably attachable to an opposite end of the air sleeve allowing for a universal sleeve that is adjustable for a range of limb size diameters.

12. An air sleeve according to claim 1, wherein the base film comprises facing sheets of film that are welded together to define the array of nodal air cells.

13. An air sleeve according to claim 1, wherein the air cell perforations vary in size, and wherein the air cell array is configured to deliver evenly distributed pressure variations without lines or ridges of high pressure.

14. An air sleeve according to claim 1, wherein the spacer fabric layer defines an air passage that permits air circulation around and through a complete length of the air sleeve.

15. An air sleeve for stimulating blood flow and providing aeration around, under and within a cast, the air sleeve comprising:

facing sheets of film that are RF welded together to define an array of nodal air cells connected via integrated plumbing channels, at least some of the air cells being perforated on a skin side of the facing sheets; and a plumbing fitting extendable through the cast and in fluid communication with the air cells via the integrated plumbing channels.

16. An air sleeve according to claim 15, further comprising a spacer fabric layer disposed on the skin side of the base film, the spacer fabric being at least partially air permeable.

17. An air sleeve according to claim 16, wherein the array of nodal air cells comprises a matrix of air cells including rows and columns, and wherein alternating ones of the nodal air cells along the rows and columns are perforated.

18. An air sleeve according to claim 17, wherein the plumbing fitting comprises a first valve in fluid communication with a first set of the alternating nodal air cells, and a second valve in fluid communication with a second set of the alternating nodal air cells.

19. A method for stimulating blood flow and providing aeration around, under and within a cast using an air sleeve including a base film with an array of nodal air cells, at least some of which are perforated on a skin side of the base film, a spacer fabric layer that is at least partially air permeable disposed on the skin side of the base film, and a valve extendable through the cast and in fluid communication with the air cells, the method comprising:

(a) connecting a pump to the valve;
 (b) inflating the air cells; and
 (c) bleeding air through the perforations and the spacer fabric layer to aerate a wearer's skin inside the case.

20. A method according to claim 19, wherein the pump is portable, and wherein the method comprises repeating steps (b)-(c) in a continuous cycle.

* * * * *